(12) United States Patent
Khoury

(10) Patent No.: US 6,618,138 B2
(45) Date of Patent: Sep. 9, 2003

(54) SCANNING FLUORESCENT SYSTEMS FOR VARIOUS DIAGNOSTIC

(76) Inventor: Jed Khoury, 33 Tanbark Rd., Sudbury, MA (US) 01776

(*) Notice: Subject to any disclaimer, the term of this patent is extended or adjusted under 35 U.S.C. 154(b) by 0 days.

(21) Appl. No.: 09/973,996

(22) Filed: Oct. 9, 2001

(65) Prior Publication Data

US 2002/0044279 A1 Apr. 18, 2002

Related U.S. Application Data

(60) Provisional application No. 60/239,833, filed on Oct. 12, 2000.

(51) Int. Cl.[7] .................................................. G01J 3/40
(52) U.S. Cl. ...................... 356/302; 356/300; 382/278; 382/165; 382/191; 382/211
(58) Field of Search ................. 356/319, 300, 356/302, 303, 305; 382/278, 165, 191, 211; 359/29, 116

(56) References Cited

U.S. PATENT DOCUMENTS 5,727,226 A * 3/1998 Blaum et al. ............... 395/800
6,023,355 A * 2/2000 Bashaw et al. ............... 359/21
6,373,967 B2 * 4/2002 Pu et al. ....................... 382/115
6,480,273 B1 * 11/2002 Brock et al. ................ 356/300

* cited by examiner

Primary Examiner—Frank G. Font
Assistant Examiner—Layla Lauchman
(74) Attorney, Agent, or Firm—Robert Nathans

(57) ABSTRACT

An angularly multiplexed store contains filters derived from prior examination of input image reference samples, a spectrum analyzer produces spectral data representing the frequency spectrum of the input image under examination, a computer produces an encoded map of the spectral data representing the input image frequency spectrum. The encoded map is transformed, inputted into the store while close match spectral correlation light beams emerge from the multiplexed store, each having an emerging angle associated with that filter within the multiplexed store producing a close match with the first transform. An array of light beam detectors and a display present images having colors that indicate the nature of the input image such as a type of cancer. An associated memory-retro-reflector arrangement displays characters naming the materials making up the input image such as types of abnormal tissue. The disclosed apparatus can have significant application in medicine, food industry, spectroscopy, material science and other various areas.

30 Claims, 1 Drawing Sheet

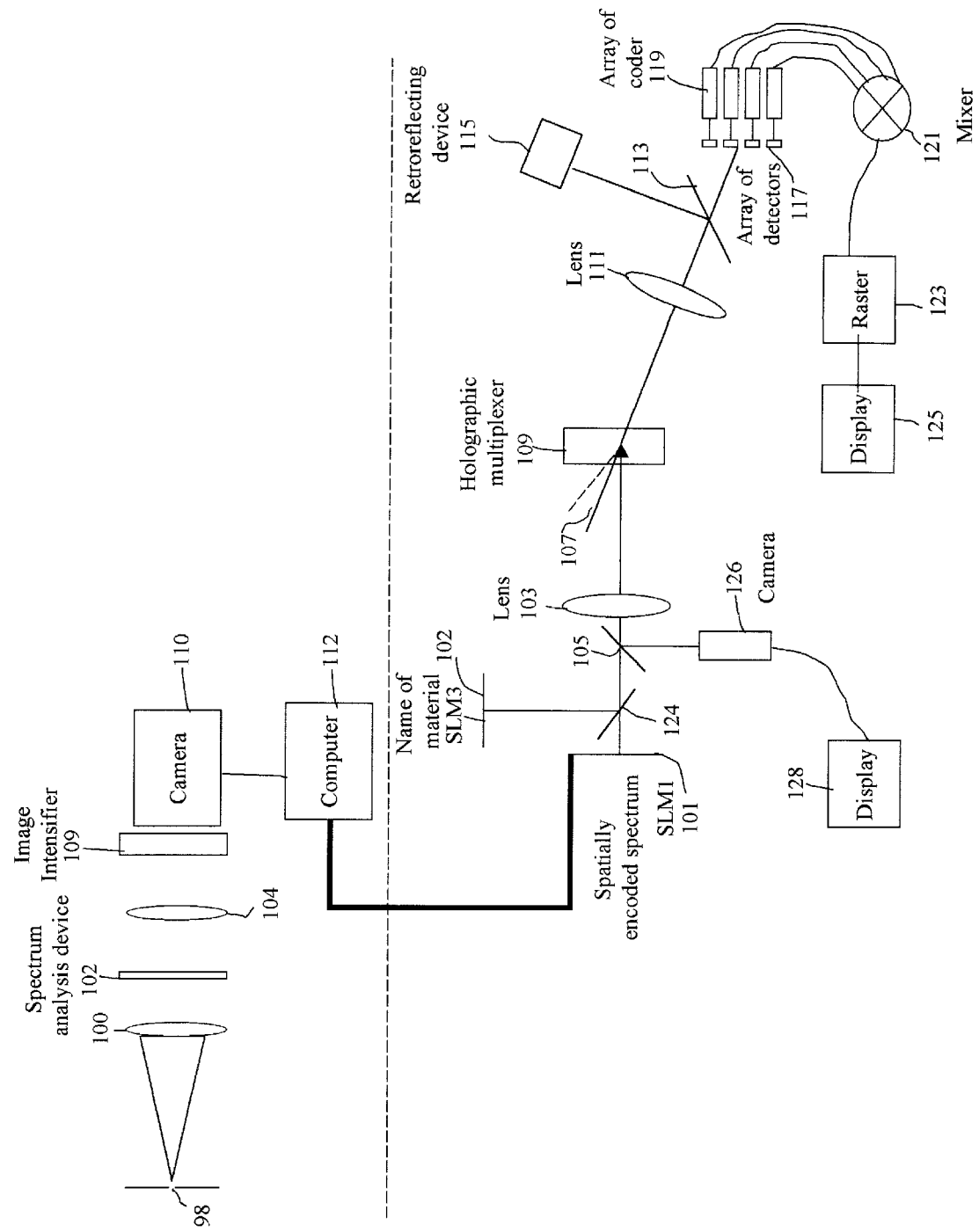

SCANNING FLUORESCENT SYSTEMS FOR VARIOUS DIAGNOSTIC

CROSS REFERENCE TO RELATED APPLICATIONS

This application claims the benefit of provisional application Ser. No. 60/239,833, filed Oct. 12, 2000.

BACKGROUND OF THE INVENTION

Recognition based on fluorescent emission (spectrum) from materials has become a very important area in recent years. See *Fluorescence Correlation Spectroscopy: Springer Series in Chemical Physics*, Vol. 65, Rigler, Rudolf; see also *Special Issue in optical Engineering Opt. Eng.* 37, 453–467 (1998). Advantageously, the spectrum of the fluorescence emitted from a certain material is a unique characteristic of that material, and can be considered as a finger print identification of it. Recognition based on fluorescence and the spectrum has been used in a variety of areas, including spectroscopy fluorescent microscopy, See R. B. Dorshow, J. E. Bugaj, B. D. Burleigh, J R. Dunean, M. A. Johnson and W. B. Jones, *"Noninvasive fluorescence detection of hepatic and renal function," Journal of Biomedical optics,* 3, 340–345 (1998), *IEEE engineering in medicine and Biology* (September and October issue 1999), *Regarding Interpretation of images see* http://creatis-www.insa-lyon.fr/recherche/thfus/demos/accueil_demos.html; Regarding DNA sequencing, biochemistry, biophysics, and cell biology analysis, biology, medical diagnostics: see *TOOLS &TECHNOLOGY Fluorescence Spectroscopy Methods Reveal Biomolecules' Dynamics* http://www.the-scientist.lib.upenn.edu/yr1995/june/tt_950612.html web site related to biology. Regarding medical diagnostics in vivo monitor hemoglobin-myoglobin oxygen saturation in localized regions, see Carol B. Murray and Gerald M. Loughlin, *"Making the most of pulse oximetry," Contemporary Pediatrics*12, 45–62 (1995).

Thus, in the past, many papers have been published in this area. The spectrum, which is emitted from the samples being examined, is collected and sent to digital processing system or serial electronic system for analysis. In most cases these digital processing systems use computational algorithms for analysis and recognition of the materials. The digital processing or serial electronic signal on full image pixel by pixel can be very time consuming.

For some applications, such as biopsy analysis, speed of processing may not be critical. However, there are other applications, for example, where a doctor needs to recognize abnormal tissues in the body at the time of the operation, or in agricultural other similar applications when a pilot needs to recognize and treat an unhealthy crop as he is in flight. Or consider the problem when an environmentalist must recognize and simultaneously treat a problem in pollution. Such problems are not easy yet to resolve in real-time.

Therefore in accordance with the present invention, I am proposing a new spatial fluorescence spectroscopic associative memory-correlator for recognition and classification. This system can be used for multipurpose applications. They include the following: (1) fluorescent microscopy (2) endoscopy (3) DNA analysis (4) all forms of spectroscopy, including optical, X-ray and -ray, neutron, electron, molecular spectroscopy. References in the solid state physics literature cite examples for the various forms of spectroscopy. For X ray spectroscopy, see for example Kittle, *Introduction to solid state physics*.

The principal applications of this system are in the medical, food, chemical and biotech industries. In the medical area, this system may be used in variety of applications involving, for example, infrared pathology for diagnostics relating to various forms of cancer such as: cervical, colon, skin, breast, brain, oral, prostate, thyroid, leukemia. In addition, this system may be used in diagnosing various neurological disorders such as alzheimer's disease, multiple sclerosis and a number of cardiovascular disorders. The use of this system can be extended further to include arthritis diagnostics because of a difference between infrared spectra of synovial fluid from healthy and diseased joints. Further, this technique may allow us to assess the effects of drugs on joint physiology, thereby providing an aid in clinical monitoring and treatment.

This system can also be used in infrared clinical chemistry for example, in the analyses of common biological fluids such as blood/serum or urine, or diagnostics of less common biofluids such as amniotic fluid, saliva or synovial fluid.

Further applications may involve infrared imaging and in-vivo spectroscopy Including (1) monitoring of tissue physiology, tissue oxygenation, respiratory status and ischemic damage. (2) In the study of calcified tissue and in dermatologic and cosmetic applications such as evaluation of fingernail health status, assessment of UV photodamaged skin, or assessment of anti-psoriatic drugs (3) In applications for critical care and reconstructive surgery or as a tool for non-invasive blood glucose determination. (4) In non-invasive near-IR spectroscopy to monitor hemoglobin-myoglobin oxygen saturation in localized regions of peripheral tissue. (5) In conjunction with a fiber-optic cable connected to the excitation source which radiated the whole heart and measured the calcium released as a function of flow to the coronary vessels. In dental treatment for detecting decay based on spectroscopic emission (*Laser Focus* February 1999, p34).

A fluorescence correlation spectroscopy technique already has been used as a diagnostics tool in various areas: (see *First Edition Fluorescence Correlation Spectroscopy: Springer Series in Chemical Physics*, Vol. 65, Rigler, Rudolf nucleic acid analysis, study of protein-ligand interaction, high throughput screening, antibunching and rotational motion, drug discovery, spatial correlations on biological surfaces, identification of alzheimer and Prion aggregation and confocal optics for single and 2-colo, flavine-enzymes.

Systems of the present invention can be also used in conjunction with Raman spectrometers. Raman spectroscopy is one of the main tools used in analysis various solid state material. These days the use of Raman spectroscopy has been extended to include the food industry (*FoodTechnology, January/Febrary* 2001, p 43), biotechnology, and the medical area. In the chemical industry, this system can be set in conjunction with the spectrometer to perform strait forward recognition of materials or compounds, thereby by eliminating the need for spectroscopic tables, or search engines based on dada base software. In food biotech industry because this industry relies on using all forms of spectroscopy including mass spectroscopy (*FoodTechnology, February* 2001, P 62) infrared spectroscopy (*FoodTechnology,January/Febrary* 2001; for *identifying foreign matter in food* p 55, or *bacteria and micro-organisim* p. 20 or *in aid of kitchen cleaning systems employing nozzles.* p 53. In metrology, material science and microelectronic industries. (See *novel laser atomic fluorescence spectrometer for environmental and biomedical analyses of heavy metals* Dergachev, Alex Y.; Mirov, Sergey B.; Pitt, Robert E.; Parmer, Keith D.; AA (Univ. of Alabama/

Birmingham; *Proc. SPIE* Vol. 2980, p. 381–389, *Advances in Fluorescence Sensing Technology III,* Richard B. Thompson; Ed. Publication Date: May 1997.

See also *Analysis of rocking curve measurements of LiF flight crystals for the objective crystal spectrometer on SPECTRUM-X-GAMMA* Halm, Ingolf; Wiebicke, Hans-Joachim; Geppert, U. R.; Christensen, Finn E.; Abdali, Salim; Schnopper, Herbert W.; AA(*Max-Planck-Institut fuer Extraterrestrische Physik*) AD(*Danish Space Research Institute*); Publication: *Proc. SPIE Vol.* 2006, p. 11–21, *EUV, X-Ray, and Gamma-Ray Instrumentation.* All of these industries use virtually all forms of spectroscopy, X ray, neutron, electron spectroscopy, spectroscopy (*Physics Today* 1996 *Buyer Guide,* A product by Amptek. Inc, Bedford Mass.). For example the Laue and Powder machines use the X ray spectroscopy to analyze the crystallographic structure of the material.

Various systems of the present invention can have two ports, one port is the correlation port, and the other port is the associative memory port. Y Owechko, *"Nonliear holographic associative memories,"* IEEE J Qantum Electronics. 25, 619–634 (1989).

The proposed system of the present invention has enormous performance power compared to any serial based fluorescence correlation spectroscopy system. This is because the proposed system allows the following features to operate simultaneously: (1) scanning line by line; (2) instantaneous spectroscopic correlation of each pixel with hundreds of templates; (3) automatic pixel noise filtering (4) automatic spectrum noise filtering. All these combined features should enable the proposed system to be working as a real time imaging system, in contrast to using the serial scanning approaches that are far slower.

SUMMARY OF PREFERRED EMBODIMENTS OF THE INVENTION

A correlation port is provided for detecting the viewed input image segmentation. An associative memory port will be used for recognition of the nature of the input image by its printed name. Thus if the input into the system is the spectrum of water, then the output of the system should display that this material is water. For medical diagnostics of tissues where it is necessary to scan all tissue on a pixel by pixel or line by line mode, it is better to use the correlation port. Whereas, if only for biopsy purposes or certain material's being sampled for identification, as is the case of many simple spectroscopic applications, it is better to use the system as associative memory. For all purpose medical applications it is preferable to use the two ports. One port is used to recognize the abnormal tissues by its name, such as a type of cancer, while the correlation port is used to display image segmentation of the tissues.

More specifically the preferred image identification system features an angularly multiplexed holographic store for storing a plurality of correlation filters derived from prior examination of a plurality of input image reference samples, an input imaging scanner for capturing an input image under examination, a spectrum analyzer for producing spectral data representing the frequency spectrum of the input image under examination, a computer for producing an encoded map of the spectral data representing the frequency spectrum of the input image under examination.

A first Fourier transform lens transforms the encoded spectral map and directs the resulting transform at the angularly multiplexed holographic store, while a second transform lens produces close match spectral correlation light beams emerging from the holographic store, each having an emerging angle with respect to the angularly multiplexed holographic store associated with that filter within the holographic store producing a close match with the resulting transform produced by the first transform lens. In case of line scanning, a linear array of light beam detectors (or a 1-D CCD array) and a display device are provided for displaying images having colors that indicate which detectors are being illuminated at any given time. In case of pixel by pixel scanning, the linear detector array should be replaced by a single pixel detector.

An associated memory data input SLM impresses data indicative of images of amplitude encoded characters upon the two-dimensional spectroscopic encoded phase map. In the case of associative memory it is preferable to use a phase map. The spectroscopic encoded phase map produced by the mapping computer or smart pixilated structure, indicates the nature of materials of portions of objects producing the input images.

A retro-reflector projects the close match spectral correlation light beams back through the holographic store, then through the first Fourier transform lens and thereafter upon a camera insensitive to light beam phase, enabling the amplitude encoded characters to be displayed by a display device coupled to said camera. The display and the feeding in of the input information into the system are somewhat limiting factors in the performance of the system, however, the processing of the information should approach the speed of light.

BRIEF DESCRIPTION OF THE DRAWINGS

The various features and advantages of the invention may be further understood by reading the following description taken in conjunction with the sole FIGURE illustrating a presently preferred embodiment of the invention.

DETAILED DESCRIPTION OF A PREFERRED EMBODIMENT OF THE INVENTION

The sole FIGURE shows a schematic diagram of the system for fluorescent diagnostics. Before we describe how this system operates in the recognition of inputted objects or targets being examined according to their spectroscopic fluorescence, let first describe the training process of this system. In the training process, a template of point source of light (that may be from a fiber) is replaced instead of the target at it's scanned pixel. The light emitted from this point source represent the spectrum of a reference sample, which will be recorded in the holographic store and later searched during the analysis of an input image under examination. The light from this point source is transferred via a lens into a plane wave. The spectrum of the light in the plane wave is analyzed via a grating or prism analyzer 102 to produce the light in vertical lines of different colors like a rainbow. This rainbow is converted to a vertical gray level dot recorded upon camera 110 via focusing lens 104a and image intensifier 108, if such intensifier is needed. Computer 112 converts the resulting two-dimensional spectroscopic map of the frequency band indicating dots into a two-dimensional complex (amplitude and phase) map of the frequency spectrum of the first reference sample that is recorded upon spatially encoded spectrum SLM 101, which in turn is Fourier transformed by FT lens 103 and the resulting filter is stored within angularly multiplexed holographic store 109.

Various algorithms provide the computer for converting the spectroscopic map into a complex encoded amplitude map. This encoded map can be purely phase, purely amplitude or the combination of both. However, for operation in the aforesaid dual mode of associative memory and correlator it preferred that the encoded map to be pure phase map. In more compact design it is possible to replace the detector and the spatial light modulator by a smart pixilated structure.

During this recordation step, reference beam generator 107 illuminates the holographic store 109 with a reference beam having a first angle with respect to the input surface of the store 109. Scene scanner 100 then scans a second reference sample and the aforesaid recordation process is repeated to record a second reference sample into store 109 but employing a reference beam from generator 107 having a slightly different illumination angle. The other reference beam is represented by the dashed arrows a1 directed at store 109 for the second sample adjacent the solid arrows a2 of the first sample, to thereby angularity multiplex the first and second input sample holographic reference filters within the store. This process continues to record hundreds of encoded spectrum correlation filters in the holographic store. Details of the operation of the angularly multiplexed holographic store correlation filters are known in the art; see the following paragraph. Perhaps a hundred or more filters of spectral phase encoded maps of 100 known cancer lesions (samples) can thus be stored in the holographic reference library. Optionally, the name of each cancer type can be impressed upon or beside each of the 100 filters of cancer lesions inputted into store 109 by inputting these names into SLM3, which causes character images of these names, for later display, to be coupled to each of the reference samples in the holographic store library by beam splitter 105. In this case, the spectral encoded map should be in phase encoded form.

To summarize the recordation process, the name of the sample type is addressed to the SLM 103 and the information from both the SLMs is combined by beam splitter 105 and recorded on an angularly multiplexed holographic store 109. The Fourier transform of the combined information interferes with the reference beam from beam generator 107, and both beams write holograms on the holographic multiplexer. Accordingly, templates of many superimposed names and spatially encoded spectrum are angularly multiplexed on the holographic multiplixer 109. For further information regarding multiplexing images on the holographic store see Fai. H. Moke, Angle-multiplexed storage of 5000 holograms in lithium niobate, Opt. Letts 18, 915–917(1993). See also Burr and F. H. Moke and Psaltis in conference on laser and electro-optics, Vol 8 of 1994 OSA technical digest series (Optical Society of America, Washington D.C., 1994 paper CMB7). Other forms of multiplexing, such as rotational multiplexing, SDF, can be employed. The spatially encoded spectrum is preferably pure phase information, while the characters representing the sample names recorded on SLM3 is preferably recorded as amplitude information.

A particular input image 101a to be analyzed such as a lesion, can now scanned pixel by pixel or line by line by scene scanner 100 and computer 112 causes its two-dimensional spectrum encoded pure phase map to be recorded upon SLM 101, and thereafter Fourier transformed by FT lens 107 and then directed at holographic store 109. The scanner can comprise two cascaded mirrors for point by point scanning. For scanning line by line only one mirror would be needed. For more details regarding various prior art scanners, see chapter 19 of "Hand Book of Optics, Volume II" edited by Michael Bass.

Each detector of linear detector array 117 now detects or pick-ups the close match spectral correlation between portions of the input image and corresponding portions of the close match reference image being correlated therewith. The output from each detector is sent to an associated color encoder of color coder array 119 and the output from all the coders are mixed together by multi-input mixer component 121, the mixer output from the mixer being sent to the raster scanner 123 and then to the display system element 125, these devices operating like a TV receiver. This operation thus produces a color encoded image of say a particular stored reference lesion that is closely correlated or matched with the spectral map of the input image being analyzed. This operation may be carried out by sequential point by point scanning or preferably by employing a cylindrical lens to capture a line at a time of the spatially encoded spectrum at SLM1. In this case, the detector array could comprise a two-dimensional array of detectors and their associated color encoders.

Since a first portion of the image of the viewed lesion could correlate with a first stored phase map filter in the holographic memory 109, and a second portion could correlate with a second phase map filter, the output displayed by display receiver 125 could have two or more colors, indicating for example a mixture of two different types of cancer, within the same lesion. Correlation between portions of the phase maps of input image being analyzed and corresponding portions of the reference phase map closely correlated therewith, will produce light beams having emerging angles which are a function of the close match filter correlated therewith. This is a result of the angle of the emerging readout beam being equal to the recordation beam, where there is a close match correlation, as is known to workers in the art. This function enables the operation of the color-coded detectors for indicating close matches of image portions.

One may consider various schemes for color coding, some of these schemes can be pure electronic hardware (2) other schemes can be hybrid of electronic and software routines.

One way for example to design the hardware color coder, is to binaraize the output signal of each one of the output detectors, then to distribute the binaraized signal of each the detector to three different signal components. These three signal components are used to address the three guns of the Green, Red, and Blue in a color TV. Before addressing these component to the TV. The signal, which corresponds for each certain color should, combined (mixed). According to this approach, the number of the mixers should be equal to the number of the detectors. In the Hybrid electronic software approach one may built an color coded image for each of the detector using Graphic User Interface (GUI) or GDI (Graphic Device Interface), then to combine (mix) the images from these detectors. These routines are available in computer languages such as C, C++, JAVA, IDL, MATLAB. An alternative approach is to encode the images from each of the detectors with a certain gray level, to combine these images and then to follow the process by a pseudocolor images processing routine. Color image processing routines can utilize RGB, but other coding schemes are available.

Regarding the associative memory function, while the output from the array of detectors 117 is used for correlation purposes, the light reflected from the retro-reflector 115 is used for associative memory purposes. In this case, the correlation output is retro-reflected via element 115, which can be either a mirror or nonlinear device such as a holographic element. The aforesaid close match correlation process beneficially generates a plane wave that is back propagated by the retroreflector into the holographic multiplexer 109. The plane wave that is read out of the Fourier transformed stored template, Bragg matches the appropriate retro-reflected correlation. The output from the holographic multiplexer is Fourier transformed via lens 107 to generate the sum of the sample names and the spatially encoded spectrum, in turn recorded by camera 126 via beam splitter 124 and displayed by display screen 128. Thus, it is recommended that the characters making up the name of each sample should be pure amplitude information and the spatially encoded spectrum should be pure phase information. Since the phase information is not detected by beam splitter 124, camera 126, and display 128, only the name of the sample will appear on the display.

It is important to understand that unlike Fourier transform image correlators of the Vander Lugt type, previously mentioned, the use of the aforesaid angularly multiplexed thick holographic store is highly beneficial due to the Bragg matched condition which makes the filter variant to shift. The variance to shift has three advantages:

(A) The variance to shift reduces the undesired effects of filter to filter noise such as fluorescent noise of other objects in the same pixel; (B) If two pixels have the exactly similar encoded spectrum but one is frequency shifted compared to the other, the shift variance sensitivity in the present invention beneficially does not allow the shifted encoded spectrum to correlate. This in contrast to correlation based on filters such as the Vander Lugt filter.

As numerous variations in the above description will occur to one skilled in the art, the scope of the invention is to be limited solely by the following terms including art recognized equivalents thereof For example, the first and second Fourier transform means could employ 1-D Fourier transforms using cylindrical lenses. Other forms of multiplexing could be employed other than angular multiplexing. For example all form of holographic multiplexing such as shift multiplexing, rotational multiplexing, wavelength multiplexing, spatial multiplexing, or syntactic discriminating function (SDF) may be employed for this purpose. Rather than being linear arrays for interpreting beam angles as in the FIGURE, the arrays of detectors could be configured by the skilled worker to interpret other various beam characteristics (e.g. degree of rotation) of the beams exiting the multiplexed filter store 109.

The SDF design may easier to implement using programmable spatial light modulator, however it does not necessarily gave good results as the holographic multiplexer, although this design may provide substantial flexibility for reconfiguration of this system.

It is well known in Fourier optics that the spherical lens operate as a 2-D Fourier transform device if one look at the light distribution at the lens focal plane. The 1-D Fourier transformation device is not simply cylindrical lens if one look at the light distribution at the lens focal plane, but should be a combination employing a spherical lens and a cascaded cylindrical lens. The cylindrical lens operates as a 1-D Fourier transform device and the spherical lens is operating as an imaging device.

In this invention I described the design of SCANNING FLUORESCENT SYSTEMS FOR VARIOUS DIAGNOSTIC purposes. In the description only the operational principles of this system were considered with out considering any compactness in the design. For commercial purposes, this system may be redesigned resulting in very compact structures, considering the following facts:

(a) Fourier transform mean (lens or convex or convex mirrors) and the spectrum analysis means (grating or prism) can be integrated together in various form, example (1) through encoding both using binary optics, (2) engraving a grating on the Fourier transform means (lens or mirror), (3) printing gratings on the Fourier transform means (lens or mirror) or any possible commination of these cases (4) using holographic means;

(b) Fourier transform means (lens or mirror) and spatial light modulator can be integrated in one device using one of the following approaches (a) fabrication of a lens, (binary optical or holographic lens) on the spatial light modulator (b) simultaneous encoding of the input information and the lens convexity on the spatial light modulator;

(c) The cylindrical lens and the spherical lens can be integrated in one optical component or through a binary optics component, or a holographic component.

I claim:

1. An image identification system comprising:
(a) a multiplexed filter store for storing a plurality of filters derived from prior examination of a plurality of input image reference samples;
(b) input imaging means for capturing an input image under examination;
(c) a spectrum analyzer for producing spectral data representing the frequency spectrum of said input image under examination;
(d) mapping means for producing a spectrum encoded map of said spectral data representing the frequency spectrum of said input image under examination;
(e) first transform means for transforming said spectrum encoded map and directing the resulting transform at said multiplexed filter store;
(f) second transform means for producing close match spectral correlation light beams emerging from said multiplexed filter store, each beam having an emerging angle with respect to said multiplexed filter store associated with that filter within said multiplexed filter store producing a close match with the resulting transform produced by said first transform means; and
(g) detector means positioned in the path of said close match spectral correlation light beams for producing an identification map that is a function of the emerging angle of said close match spectral correlation light beams.

2. Apparatus of claim 1 wherein said detector means comprises an array of detectors and a display device coupled to said array of detectors for displaying images that indicate which detectors are being illuminated at any given time.

3. Apparatus of claim 2 wherein said detector means includes color coding means coupled to said array of detectors and to said display device for causing said display device to produce color coded images of said input image under examination.

4. Apparatus of claim 2 including raster scanning means coupled between said array of color coders and said display device.

5. Apparatus of claim 1 further including associated memory data input means for impressing data indicative of images of amplitude encoded characters with said spectrum encoded map produced by said mapping means, indicating the nature of materials of portions of objects producing said input images captured by said input imaging means.

6. Apparatus of claim 2 further including associated memory data input means for impressing data indicative of images of amplitude encoded characters with said spectrum encoded map produced by said mapping means, indicating the nature of materials of portions of objects producing said input images captured by said input imaging means.

7. Apparatus of claim 3 further including associated memory data input means for impressing data indicative of images of amplitude encoded characters with said spectrum encoded map produced by said mapping means, indicating the nature of materials of portions of objects producing said input images captured by said input imaging means.

8. Apparatus of claim 4 further including associated memory data input means for impressing data indicative of images of amplitude encoded characters with said spectrum encoded map produced by said mapping means, indicating the nature of materials of portions of objects producing said input images captured by said input imaging means.

9. Apparatus of claim 5 including retro-reflector means for retro-reflecting said close match spectral correlation light beams back through said multiplexed filter store, then through said first transform means and thereafter upon a camera, enabling said amplitude encoded characters to be displayed by a display device coupled to said camera.

10. Apparatus of claim 6 including retro-reflector means for retro-reflecting said close match spectral correlation light beams back through said multiplexed filter store, then through said first transform means and thereafter upon a camera, enabling said amplitude encoded characters to be displayed by a display device coupled to said camera.

11. Apparatus of claim 7 including retro-reflector means for retro-reflecting said close match spectral correlation light beams back through said multiplexed filter store, then through said first transform means and thereafter upon a camera, enabling said amplitude encoded characters to be displayed by a display device coupled to said camera.

12. Apparatus of claim 8 including retro-reflector means for retro-reflecting said close match spectral correlation light beams back through said multiplexed filter store, then through said first transform means and thereafter upon a camera, enabling said amplitude encoded characters to be displayed by a display device coupled to said camera.

13. Apparatus of claim 3 including raster scanning means coupled between said array of detectors and said display device.

14. An image identification system comprising:
(a) a multiplexed holographic filter store for storing a plurality of filters derived from prior examination of a plurality of input image reference samples;
(b) input imaging means for capturing an input image under examination;
(c) a spectrum analyzer for producing spectral data representing the frequency spectrum of said input image under examination;
(d) mapping means for producing a spectrum phase encoded map of said spectral data representing the frequency spectrum of said input image under examination;
(f) first transform means for transforming said spectrum phase encoded map and directing the resulting transform at said multiplexed holographic filter store;
(f) second transform means for producing close match spectral correlation light beams emerging from said multiplexed filter store, each beam having an emerging angle with respect to said multiplexed filter store associated with that filter within said multiplexed filter store producing a close match with the resulting transform produced by said first transform means; and
(g) detector means positioned in the path of said close match spectral correlation light beams for producing an identification map that is a function of the emerging angle of said close match spectral correlation light beams.

15. Apparatus of claim 14 wherein said detector means comprises an array of detectors and a display device coupled to said array of detectors for displaying images that indicate which detectors are being illuminated at any given time.

16. Apparatus of claim 15 wherein said detector means includes color coding means coupled to said array of detectors and to said display device for causing said display device to produce color coded images of said input image under examination.

17. Apparatus of claim 15 including raster scanning means coupled between said array of detectors and said display device.

18. Apparatus of claim 14 further including associated memory data input means for impressing data indicative of images of amplitude encoded characters upon said spectrum phase encoded map produced by said mapping means, indicating the nature of materials of portions of objects producing said input images captured by said input imaging means.

19. Apparatus of claim 15 further including associated memory data input means for impressing data indicative of images of amplitude encoded characters upon said spectrum phase encoded ma map produced by said mapping means, indicating the nature of materials of portions of objects producing said input images captured by said input imaging means.

20. Apparatus of claim 16 further including associated memory data input means for impressing data indicative of images of amplitude encoded characters upon said spectrum phase encoded ma produced by said mapping means, indicating the nature of materials of portions of objects producing said input images captured by said input imaging means.

21. Apparatus of claim 17 further including associated memory data input means for impressing data indicative of images of amplitude encoded characters upon said spectrum phase encoded ma produced by said mapping means, indicating the nature of materials of portions of objects producing said input images captured by said input imaging means.

22. Apparatus of claim 18 including retro-reflector means for retro-reflecting said close match spectral correlation light beams back through said multiplexed filter store, then through said first transform means and thereafter upon a camera insensitive to light beam phase, enabling said amplitude encoded characters to be displayed by a display device coupled to said camera.

23. Apparatus of claim 19 including retro-reflector means for retro-reflecting said close match spectral correlation light beams back through said multiplexed filter store, then through said first transform means and thereafter upon a camera, enabling said amplitude encoded characters to be displayed by a display device coupled to said camera.

24. Apparatus of claim 20 including retro-reflector means for retro-reflecting said close match spectral correlation light beams back through said multiplexed filter store, then through said first transform means and thereafter upon a camera, enabling said amplitude encoded characters to be displayed by a display device coupled to said camera.

25. Apparatus of claim 21 including retro-reflector means for retro-reflecting said close match spectral correlation light beams back through said multiplexed filter store, then through said first transform means and thereafter upon a camera, enabling said amplitude encoded characters to be displayed by a display device coupled to said camera.

26. Apparatus of claim 16 including raster scanning means coupled between said array of detectors and said display device.

27. An image identification system comprising:
(a) a multiplexed filter store for storing a plurality of filters derived from prior examination of a plurality of input image reference samples;
(b) input imaging means for capturing an input image under examination;
(c) a spectrum analyzer for producing spectral data representing the frequency spectrum of said input image under examination;
(d) mapping means for producing a spectrum encoded map of said spectral data representing the frequency spectrum of said input image under examination;
(e) first transform means for transforming said spectrum encoded map and directing the resulting transform at said multiplexed filter store;
(f) second transform means for producing close match spectral correlation light beams emerging from said multiplexed filter store, each beam having particular beam characteristics with respect to said multiplexed filter store associated with that filter within said multiplexed filter store producing a close match with the resulting transform produced by said first transform means; and
(g) detector means positioned in the path of said close match spectral correlation light beams for producing an identification map that is a function of the beam characteristics of said close match spectral correlation light beams.

28. Apparatus of claim 27 wherein said spectrum encoded map is pure phase encoded.

29. Apparatus of claim 27 wherein said multiplexed filter store is a holographic multiplexed filter store.

30. Apparatus of claim 28 wherein said multiplexed filter store is a holographic multiplexed filter store.

* * * * *